(12) United States Patent
Girault et al.

(10) Patent No.: US 9,456,666 B2
(45) Date of Patent: Oct. 4, 2016

(54) ADJUSTMENT DEVICE FOR A PORTABLE ELEMENT COMPRISING WIRE-SHAPED ELEMENTS

(71) Applicant: ZEDEL, Crolles (FR)

(72) Inventors: Eric Girault, Annecy (FR); Grégory Martin, Les Adrets (FR)

(73) Assignee: ZEDEL, Crolles (FR)

( * ) Notice: Subject to any disclaimer, the term of this patent is extended or adjusted under 35 U.S.C. 154(b) by 203 days.

(21) Appl. No.: 14/159,889

(22) Filed: Jan. 21, 2014

(65) Prior Publication Data

US 2014/0201953 A1    Jul. 24, 2014

(30) Foreign Application Priority Data

Jan. 21, 2013  (FR) ...................................... 13 00129

(51) Int. Cl.
| | |
|---|---|
| A44B 99/00 | (2010.01) |
| F21V 33/00 | (2006.01) |
| A61F 9/02 | (2006.01) |
| F21V 21/084 | (2006.01) |
| A63B 33/00 | (2006.01) |
| G02C 3/00 | (2006.01) |

(52) U.S. Cl.
CPC ................ *A44B 99/00* (2013.01); *A61F 9/027* (2013.01); *F21V 33/0008* (2013.01); *A63B 33/002* (2013.01); *F21V 21/084* (2013.01); *G02C 3/003* (2013.01); *Y10T 24/392* (2015.01)

(58) Field of Classification Search
CPC . A44B 99/00; F21V 33/0008; F21V 21/084; A61F 9/027; Y10T 24/392; Y10T 24/2164; G02C 3/003; A63B 33/002
USPC ..................................................... 2/417, 418
See application file for complete search history.

(56) References Cited

U.S. PATENT DOCUMENTS

| | | | | |
|---|---|---|---|---|
| 2,291,089 A | * | 7/1942 | Okun ..................... | A44B 15/00 24/115 H |
| 3,450,467 A | * | 6/1969 | Phillips ................... | A44C 5/22 351/156 |
| 5,210,912 A | * | 5/1993 | Hoefkes .................. | F16G 11/00 24/129 C |
| 5,303,428 A | * | 4/1994 | Pernicka ................. | A61F 9/027 2/428 |
| 5,406,340 A | * | 4/1995 | Hoff ....................... | A61F 9/027 2/452 |
| 5,727,259 A | * | 3/1998 | Kawamata ......... | A44B 11/2592 2/452 |
| 6,321,391 B1 | * | 11/2001 | Basso ..................... | A61F 9/027 128/858 |

(Continued)

FOREIGN PATENT DOCUMENTS

EP         2 481 981 A1   8/2012

*Primary Examiner* — Robert J Sandy
*Assistant Examiner* — Louis Mercado
(74) *Attorney, Agent, or Firm* — Oliff PLC

(57) ABSTRACT

The adjustment device for a portable element includes: a first and second pair of first and second wire-shaped elements; a first adjustment unit mounted mobile on the first pair of wire-shaped elements and configured to: define two deviation paths of the first pair of wire-shaped elements and to separate the first and second wire-shaped elements of the first pair by a first distance X1, and define a first mechanical coupling means with the second pair of wire-shaped elements; and a second adjustment unit mounted mobile on the second pair of wire-shaped elements and configured to: define two deviation paths of the second pair of wire-shaped elements and to separate the first and second wire-shaped elements of the second pair by a second distance X2, and define a first mechanical coupling means with the first pair of wire-shaped elements.

13 Claims, 2 Drawing Sheets

(56) References Cited

U.S. PATENT DOCUMENTS

| | | | |
|---|---|---|---|
| 6,817,068 B2 * | 11/2004 | Cleary | A61F 9/027 2/426 |
| 2004/0128745 A1 | 7/2004 | Cleary et al. | |
| 2005/0103344 A1 * | 5/2005 | Cheng | A41D 13/1161 128/206.13 |
| 2006/0059608 A1 | 3/2006 | Difilippo | |
| 2007/0046889 A1 * | 3/2007 | Miller | G02C 3/003 351/62 |

* cited by examiner

ADJUSTMENT DEVICE FOR A PORTABLE ELEMENT COMPRISING WIRE-SHAPED ELEMENTS

BACKGROUND OF THE INVENTION

The present invention relates to an adjustment device for a portable element, and more particularly to an improved adjustment device for a portable element comprising wire-shaped elements and enabling simple, fast and efficient adjustment.

STATE OF THE ART

Adjustment devices for portable elements are very widely used in particular in the sporting field. This is the case in particular of devices for ensuring correct positioning of headlamps, snow goggles or a diving mask, swimming goggles, etc.

Adjustment devices available at present on the market, in particular those for snow goggles, are in the form of a single unit enabling adjustment of the length of a strap passing around the user's head and performing securing of the portable element. The adjustment unit comprises a slide path enabling the strap to be diverted and a fixing area of said strap. Associated with the adjustment unit, a ring enables the strap, passing through the ring, to make a loop between said ring and the adjustment unit. The separating distance between the ring and the adjustment unit enables the length of the strap to be adjusted. This type of device presents the drawback of not being very practical when the user wishes to modify the adjustment without removing the portable element while continuing his or her activity. Indeed, to adjust this type of device, the user has to hold the sliding strand in the single adjustment unit and make the adjustment unit slide on the latter. The user therefore first has to determine which of the two elements present on the strap is the adjustment unit and then which of the strands is sliding on the adjustment unit. He or she then has to perform sliding of the adjustment unit along said sliding strand. Such an adjustment is therefore relatively long and laborious when the user is performing his or her activity, all the more so as the adjustment unit and the ring are generally positioned at the back of the head.

Adjustment devices for portable elements of swimming or diving goggle type, also exist in the form of two adjustment units arranged specifically on each side of the portable element, on the support of said element itself. These types of device are sometimes provided with a particular headstrap, that is generally silicone-based, comprising a splitting zone fixed at the level of the occipital part of the head. Such a strap achieves good securing of the portable element, but adjustment of the strap length of such a device remains difficult to perform. In particular, the user tends to exert a stronger pull on the adjustment strap on one side than on the other, which results in non-symmetric adjustment of the splitting zone with respect to the sagittal plane. The splitting zone, which is incorrectly positioned, then loses its efficiency in terms of securing of the portable element.

Furthermore, devices of the prior art generally comprise specific straps of flexible woven strip or silicone-based strap type, which it is difficult to replace when they are worn or damaged.

OBJECT OF THE INVENTION

The present invention tends to resolve the shortcomings of traditional adjustment devices by proposing an improvement for adjustment devices for portable elements.

According to the invention, this object is achieved by means of an adjustment device for a portable element comprising:
- a first and a second pair of a first and a second wire-shaped elements;
- a first adjustment unit mounted mobile on the first pair of wire-shaped elements and configured to:
  - define two deviation paths of the first pair of wire-shaped elements and to separate the first and second wire-shaped elements of the first pair by a first distance X1,
  - define a first mechanical coupling means with the second pair of wire-shaped elements;
- a second adjustment unit mounted mobile on the second pair of wire-shaped elements and configured to:
  - define two deviation paths of the second pair of wire-shaped elements and to separate the first and second wire-shaped elements of the second pair by a second distance X2,
  - define a first mechanical coupling means with the first pair of wire-shaped elements.

BRIEF DESCRIPTION OF THE DRAWINGS

Other advantages and features will become more clearly apparent from the following description of particular embodiments of the invention given for non-restrictive example purposes only and represented in the appended drawings, in which.

DESCRIPTION OF PARTICULAR EMBODIMENTS

Figure 1:
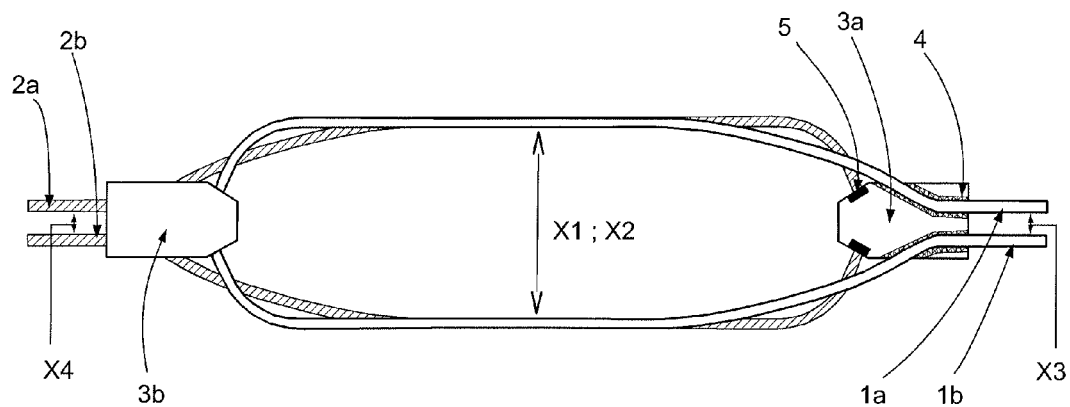
FIG. 1 schematically illustrates a view of an embodiment of the device, said view in particular presenting one of the main surfaces of one of the adjustment units (left) and a longitudinal cross-section parallel to the plane of the main surfaces of the other of the adjustment units (right)

As illustrated schematically in FIG. 1, the adjustment device for a portable element comprises a first and a second pair, respectively 1 and 2, of first and second wire-shaped elements (respectively 1a and 1b, 2a and 2b).

What is meant by "wire-shaped element" is any longitudinal flexible element having a length that is much larger than its diameter or than its width. It can for example be a cord of any diameter. Preferably, the wire-shaped element is configured to present a certain elasticity. Such wire-shaped elements present the advantage of being easily fixable and replaceable.

The adjustment device further comprises two adjustment units 3, first adjustment unit 3a being mounted mobile on the first pair of wire-shaped elements 1 and configured to:

define two deviation paths 4 of the first pair of wire-shaped elements 1 and to separate the first and second wire-shaped elements of first pair 1 by a first distance X1, define a first mechanical coupling means 5 with the second pair of wire-shaped elements 2, and second adjustment unit 3b mounted mobile on the second pair of wire-shaped elements 2 and configured to:

define two deviation paths 4 of the second pair of wire-shaped elements 2 and to separate the first and second wire-shaped elements of second pair 2 by a second distance X2, define a first mechanical coupling means 5 with the first pair of wire-shaped elements 1.

Such a device enables quick adjustment that is able to be performed even when the user is equipped with the portable element and is for example performing a physical activity. The user simply has to move the adjustment units towards one another or on the contrary move them away from one another to obtain an optimum adjustment of the length of the device.

What is meant by "deviation path" is any means enabling the wire-shaped element to be made to pass from a first plane to a second plane, the two planes being able to be offset horizontally, vertically and/or laterally. The deviation path is configured to prevent uncontrolled sliding of adjustment unit 3 along the wire-shaped element when the wire-shaped element is stretched on each side of adjustment unit 3. The deviation path induces a modification of the trajectory of the wire-shaped element. Thus, when a tension is applied on the wire-shaped element on one side of adjustment unit 3 only, the wire-shaped element slides in deviation path 4. When the same tension is applied on the wire-shaped element on both sides of adjustment unit 3, the wire-shaped element remains fixed and no longer slides in deviation path 4. This function is enhanced by the fact that there are two deviation paths per adjustment unit. Each wire-shaped element passes in a dedicated deviation path.

The first distance X1 between the first and second wire-shaped elements of first pair 1 and the second distance X2 between the first and second wire-shaped elements of second pair 2 represents the distances separating the first and second wire-shaped elements between adjustment units 3. Such a separating distance of the wire-shaped elements between the adjustment units thus ensures excellent securing of the portable element in particular due to double pressing of the separated wire-shaped elements. According to a preferred embodiment, this separating distance is situated opposite the portable element. For example purposes, when the portable element is worn on the individual's forehead or face, the separating distance is then positioned at the rear of the head. The double pressing induced by the separating distance is advantageously such that each wire-shaped element of any one pair is positioned symmetrically on each side of the plane passing through the portable element, said plane being perpendicular to the sagittal plane when the portable element is placed on the individual's face or forehead. Distances X1 and X2 are advantageously identical.

According to a preferred embodiment, deviation paths 4 of an adjustment unit 3 are configured to separate the first and second wire-shaped elements of the same pair by a distance X (respectively X3 for first pair 1 and X4 for second pair 2). The separating distances X3 and X4 correspond to the separating distance of the wire-shaped elements of the same pair existing between the wire-shaped elements connecting an adjustment unit to the portable element. Such a separation of the wire-shaped elements enables improved sliding of the wire-shaped elements in the deviation paths when said wire-shaped elements are not simultaneously under tension on each side of deviation path 4. Distances X3 and X4 are advantageously identical.

Figure 2:
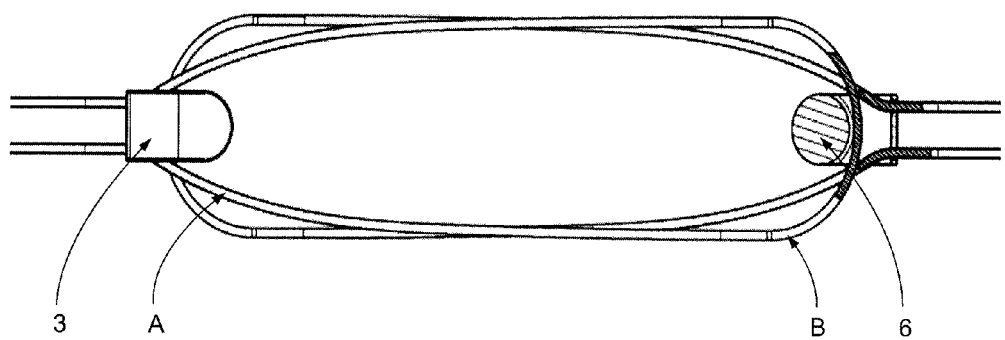
FIG. 2 schematically illustrates a view of another embodiment of the device, said view in particular presenting one of the main surfaces of one of the adjustment units (left) and a longitudinal cross-section parallel to the plane of the main surfaces of the other of the adjustment units (right)
Figure 3:
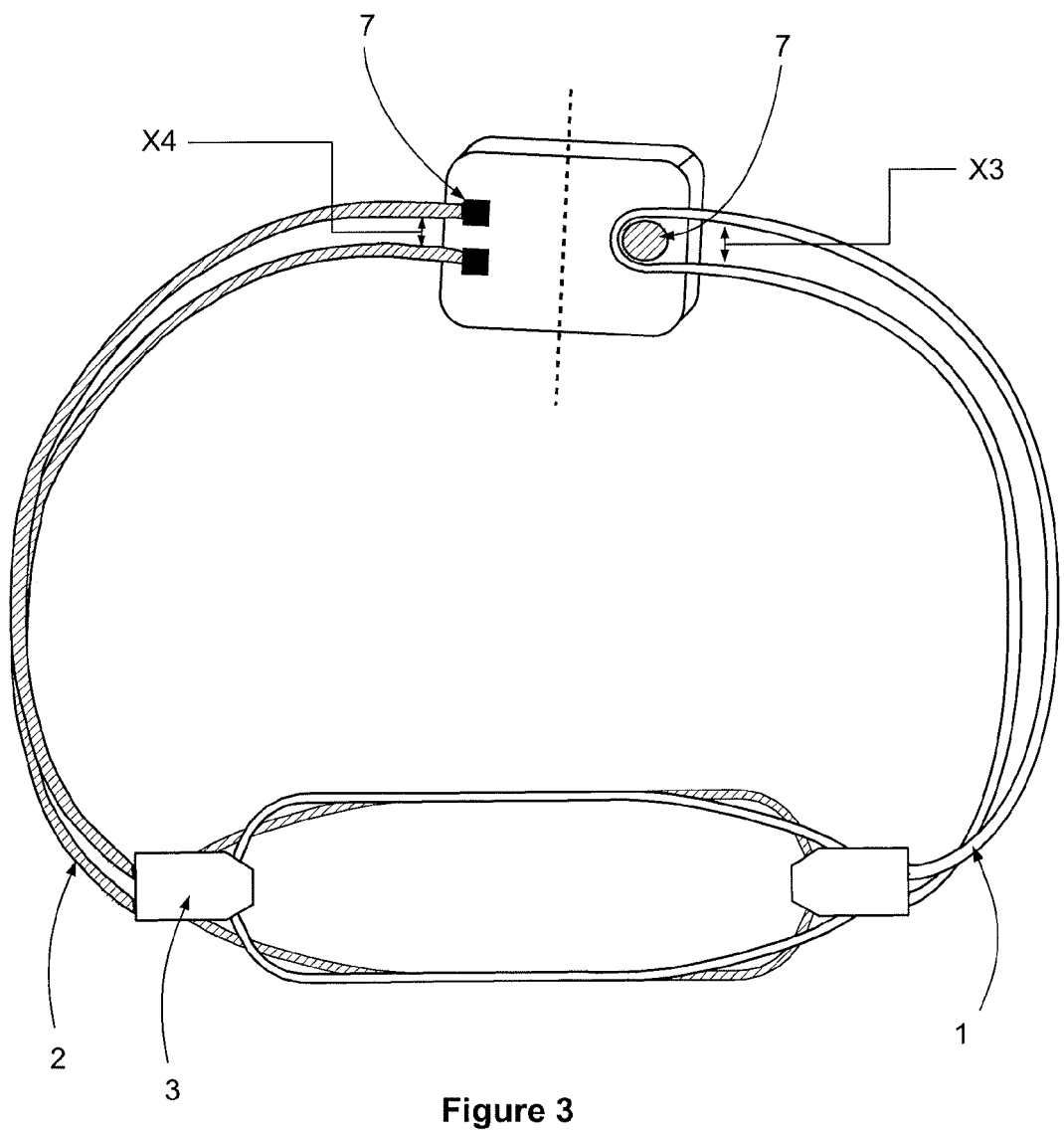
FIG. 3 schematically illustrates a view of another embodiment of the device, said view in particular presenting a longitudinal cross-section parallel to the plane of the main surfaces of the portable element and illustrating an embodiment of the second mechanical coupling means 7 (left) and a longitudinal cross-section parallel to the plane of the main surfaces of the portable element and illustrating another embodiment of the second mechanical coupling means 7 (right).

For example purposes and as illustrated in FIGS. 1 and 2, the deviation path can consist in a pass-through hole comprised in the thickness of the adjustment unit, said hole connecting a first lateral side of the adjustment unit with an adjacent second lateral side of this same adjustment unit. According to an advantageous embodiment, in particular when the portable element is a headlamp, one of the main sides of the adjustment unit corresponds to the side in contact with the head or a helmet, the other of the main sides being parallel to the latter and positioned in a rear plane. The lateral sides of the adjustment unit correspond to the sides connecting the two main sides to one another.

Each adjustment unit 3 also comprises mechanical coupling means 5. Coupling between a wire-shaped element and an adjustment unit 3 can be performed by any means known to the person skilled in the art, for example by knotting, sewing, soldering or sticking techniques. Coupling by means of one or more knots presents the advantage of making the wire-shaped elements easy to replace when they are damaged. It is possible to have a fixed mechanical coupling or a mechanical coupling enabling each adjustment unit to be mounted mobile on a pair of wire-shaped elements.

Adjustment units 3 can be of any type and of any shape. In particular, they can be made from plastic or from metal. Preferably, the adjustment units present two main sides as defined in the foregoing and at least one lateral side joining said main sides to one another. The two adjustment units are advantageously identical.

According to a preferred embodiment, the portable element is configured to:

define a second mechanical coupling means 7 of the first pair of wire-shaped elements 1 and separate the first and second wire-shaped elements of first pair 1 by a third distance X3, define a second mechanical coupling means 7 with the second pair of wire-shaped elements 2 and to separate the first and second wire-shaped elements of second pair 2 by a fourth distance X4.

Such a separation of the wire-shaped elements enables better sliding of the wire-shaped elements in the deviation paths when said wire-shaped elements are not under tension simultaneously on each side of deviation path 4.

Advantageously, the latter embodiment is associated with the previously described embodiment in which deviation paths 4 of an adjustment unit 3 are configured to separate the first and second wire-shaped element of the same pair by a distance X (respectively X3 for first pair 1 and X4 for second pair 2). Distances X3 and X4 are advantageously identical.

According to a preferred embodiment of the device and as illustrated in FIG. 2, the first and second pairs of wire-shaped elements, respectively 1 and 2, each form a single wire-shaped element, respectively A and B, and mechanical coupling means 5 of each adjustment unit 3 form a return means 6 for one of wire-shaped elements A or B. Wire-shaped element A or B is thus fitted sliding on each of the adjustment units. Advantageously, the return means are configured to increase separating distances X3, X4 with respect to separating distances X1 and X2. By means of the return means, the wire-shaped element advantageously moves in a direction parallel to the direction defined by the wire-shaped element between the portable element and the adjustment unit.

According to a preferred embodiment, the return mean 6 is configured to enable wire-shaped element A or B to form a loop having a width that is appreciably equal to distance X3 for wire-shaped element A and X4 for wire-shaped element B.

According to a particularly preferred embodiment of the device, the wire-shaped elements are of the same length. Such a device thus enables symmetrical adjustment of the portable element. The tension exerted by the two pairs of wire-shaped elements on both sides of the portable element is then always of the same intensity, guaranteeing optimum use-convenience. Symmetrical positioning of adjustment units 3 with respect to the vertical plane passing through the portable element also enables the portable element to be kept in place even when the user is adjusting the length of the device. Advantageously, said vertical plane passing through the portable element corresponds to the sagittal plane when the portable element is positioned on the face or on the forehead.

According to a preferred embodiment, the wire-shaped elements form a continuous loop. The portable element can then be fitted sliding on said continuous loop.

According to an advantageous embodiment, the portable element is a headlamp.

The portable element can be configured to be placed on the head, a helmet, an arm or another element. Preferably, the adjustment device associated with the portable element is configured to be placed on the user's head or on a helmet.

In comparison with fixing by means of a strap, the wire-shaped elements provide a greater ease of use as the surface between the wire-shaped elements can easily vary.

The invention claimed is:

1. An adjustment device for a portable element comprising:
    a first pair of wire-shaped elements with a first and a second wire-shaped element;
    a second pair of wire-shaped elements with a first and a second wire-shaped element;
    a first adjustment unit mounted mobile on the first pair of wire-shaped elements and configured to:
        define two deviation paths of the first pair of wire-shaped elements and to separate the first and second wire-shaped elements of the first pair by a first distance X1,
        define a first mechanical coupler with the second pair of wire-shaped elements; and
    a second adjustment unit mounted mobile on the first pair of wire-shaped elements and configured to:
        define two deviation paths of the second pair of wire-shaped elements and to separate the first and second wire-shaped elements of the second pair by a second distance X2,
        define a first mechanical coupler with the first pair of wire-shaped elements,
    the first wire-shaped element of the first pair of wire-shaped elements passes through the first adjustment unit from a first side of the first adjustment unit to an opposite second side of the first adjustment unit,
    the second wire-shaped element of the second pair of wire-shaped elements passes through the first adjustment unit from the first side of the first adjustment unit to the opposite second side of the first adjustment unit,
    wherein at least one of the first pair and the second pair of the wire-shaped elements forms a continuous loop, and
    the first distance X1 is measured on the first side of the first adjustment unit.

2. The adjustment device for the portable element according to claim 1, wherein:
    the first and second pairs of wire-shaped elements each form a single wire-shaped element, and
    the mechanical coupler of each adjustment unit form a return means for one of the wire-shaped elements, wherein each single wire-shaped element has two ends mechanically coupled to a connector.

3. The adjustment device for the portable element according to claim 1, wherein the first pair and the second pair of the wire-shaped elements are of a same length.

4. The adjustment device for the portable element according to claim 1, wherein the portable element comprises a headlamp.

5. An adjustment device for a portable element comprising:
    a first pair of wire-shaped elements with a first and a second wire-shaped element;
    a second pair of wire-shaped elements with a first and a second wire-shaped element;
    a first adjustment unit mounted mobile on the first pair of wire-shaped elements and configured to:
        define two deviation paths of the first pair of wire-shaped elements and to separate the first and second wire-shaped elements of the first pair by a first distance X1,
        define a first mechanical coupler with the second pair of wire-shaped elements; and
    a second adjustment unit mounted mobile on the first pair of wire-shaped elements and configured to:
        define two deviation paths of the second pair of wire-shaped elements and to separate the first and second wire-shaped elements of the second pair by a second distance X2,
        define a first mechanical coupler with the first pair of wire-shaped elements,
    wherein at least one of the first pair and the second pair of the wire-shaped elements forms a continuous loop.

6. The adjustment device for the portable element according to claim 5, wherein the portable element is configured to:
    define a second mechanical coupler with the first pair of wire-shaped elements and to separate the first and second wire-shaped elements of the first pair by a third distance X3, wherein the distance X3 is measured on another side of the first adjustment unit, and
    define a second mechanical coupler with the second pair of wire-shaped elements and to separate the first and second wire-shaped elements of the second pair by a fourth distance X4, wherein the distance X4 is measured on another side of the second adjustment unit.

7. The adjustment device for the portable element according to claim 5, wherein:
    the first and second pairs of wire-shaped elements each form a single wire-shaped element, and
    the mechanical coupler of each adjustment unit form a return means for one of the wire-shaped elements, wherein each single wire-shaped element has two ends mechanically coupled to a connector.

8. The adjustment device for the portable element according to claim 5, wherein the first pair and the second pair of the wire-shaped elements are of a same length.

9. The adjustment device for the portable element according to claim 8, wherein the portable element comprises a headlamp.

10. An adjustment device for a portable element comprising:
a first pair of wire-shaped elements with a first and a second wire-shaped element;
a second pair of wire-shaped elements with a first and a second wire-shaped element;
a first adjustment unit mounted mobile on the first pair of wire-shaped elements and configured to:
define two deviation paths of the first pair of wire-shaped elements and to separate the first and second wire-shaped elements of the first pair by a first distance X1,
define a first mechanical coupler with the second pair of wire-shaped elements; and
a second adjustment unit mounted mobile on the first pair of wire-shaped elements and configured to:
define two deviation paths of the second pair of wire-shaped elements and to separate the first and second wire-shaped elements of the second pair by a second distance X2,
define a first mechanical coupler with the first pair of wire-shaped elements,
the first wire-shaped element of the first pair of wire-shaped elements passes through the first adjustment unit from a first side of the first adjustment unit to a second side of the first adjustment unit,
the second wire-shaped element of the second pair of wire-shaped elements passes through the first adjustment unit from the first side of the first adjustment unit to the second side of the first adjustment unit, wherein at least one of the first pair and the second pair of the wire-shaped elements forms a continuous loop, and
the first distance X1 is measured on the first side of the first adjustment unit.

11. The adjustment device for the portable element according to claim 10, wherein:
the first and second pairs of wire-shaped elements each form a single wire-shaped element, and
the mechanical coupler of each adjustment unit form a return means for one of the wire-shaped elements, wherein each single wire-shaped element has two ends mechanically coupled to a connector.

12. The adjustment device for the portable element according to claim 10, wherein the first pair and the second pair of the wire-shaped elements are of a same length.

13. The adjustment device for the portable element according to claim 10, wherein the portable element comprises a headlamp.

* * * * *